United States Patent [19]

Keasling

[11] 4,269,840

[45] * May 26, 1981

[54] CERTAIN 7-(β-PHENYL-β-HYDROXYETHYLAMINO-PROPYL)-THEOPHYLLINES AS LIPOLYSIS PROMOTERS

[75] Inventor: Hugh H. Keasling, Modesto, Calif.

[73] Assignee: Shell Oil Company, Houston, Tex.

[*] Notice: The portion of the term of this patent subsequent to May 26, 1998, has been disclaimed.

[21] Appl. No.: 111,736

[22] Filed: Jan. 14, 1980

[51] Int. Cl.$^3$ .............................................. A61K 31/52

[52] U.S. Cl. .................................................. 424/253
[58] Field of Search .......................................... 424/253

[56] References Cited

U.S. PATENT DOCUMENTS 3,728,346  4/1973  Klingler ............................ 424/253

Primary Examiner—Frederick E. Waddell

[57] ABSTRACT

Certain 7-(β-phenyl-β-hydroxyethylaminopropyl)-theophyllines promote lipolysis in swine.

1 Claim, No Drawings

CERTAIN 7-(β-PHENYL-β-HYDROXYETHYLAMINOPROPYL)-THEOPHYLLINES AS LIPOLYSIS PROMOTERS

DESCRIPTION OF THE INVENTION

It has been found that lipolysis in swine is promoted by certain 7-(β-phenyl-β-hydroxyethylaminopropyl)-theophyllines, of the formula:

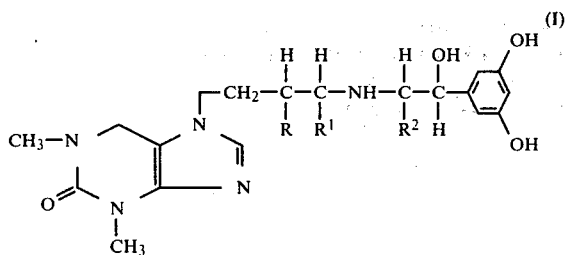

wherein both of R and $R^1$ are hydrogen, or one is methyl or hydroxyl and the other is hydrogen, and $R^2$ is hydrogen or methyl, and their physiologically acceptable acid addition salts.

These compounds also can be named as β-phenyl-β-hydroxyethylaminopropyl-3,7-dihydro-1,3-dimethyl-1H-purine-2,6-diones.

Suitable salts are those of such acids as acetic, succinic, maleic, fumaric, propionic, citric, lactic, hydrochloric, sulfuric and phosphoric acids.

Included in the invention are the individual optically active isomers, and diastereomers, as well as mixtures thereof, that promote lipolysis.

The compounds of Formula I are known: they, and methods for their preparation, are described in U.S. Pat. No. 3,728,346.

The compounds of Formula I have been found to promote—i.e., stimulate—lipolysis in swine tissue. The manner in which they cause this effect has not been established. Their effectiveness for this purpose has been ascertained by the following procedure.

A mixture of (a) 150 milligrams of slices of pig adipose tissue, approximately 0.3 millimeter thick, (b) 3 milliliters of a Krebs-Ringer bicarbonate solution, pH=7.4, containing one-half the usual calcium ion concentration, 4% fatty acid-free bovine serum albumin, 6.6 milligrams of L-ascorbic acid per milliliter, 2 milligrams of glucose per milliliter, and (c) sufficient of a solution or suspension of the test compound in dimethyl sulfoxide (DMSO), so that the final DMSO concentration in the mixture was 5%, and the test compound was present at a concentration of one microgram per milliliter of the mixture was incubated for 90 minutes at 37° C. Two replicates, taken from the tissue of one pig, were tested. The rate of lipolysis was determined by titration of the fatty acids that had been released to the medium: the tissue was removed by filtration through cheesecloth; to 0.5 milliliter of the filtrate was added 0.5 milliliter of 0.9% sodium chloride solution and 5 milliliters of a solution consisting of (by volume) 40 parts of isopropanol, 10 parts of heptane and 1 part of 1 N sulfuric acid. The mixture was allowed to stand for 5 minutes at room temperature. Then 3 milliliters of heptane and 2 milliliters of water were added. The mixture was shaken for 10 minutes, then was held until the liquid phases separated. Duplicate 1.5 milliliter aliquots of the upper phase were titrated with tetra N-butyl ammonium hydroxide, using 0.5 milliliter of methanolic Phenol Red as indicator. The basal rate of lipolysis (no test compound present) was subtracted. Test compound activity was expressed as the percent of maximal activity, estimated for each test as the activity in the presence of 16 micromolar epinephrine (L-epinephrine bitartrate). Each test compound was independently evaluated twice using tissue from two different pigs, and the percent of maximal activity indicated is the average of the two experiments.

The hydrochloride salts of the following individual species of the compounds of Formula I were tested. (For simplification, the species are characterized in terms of Formula I.):

| Test Compound No. | R | $R^1$ | $R^2$ |
|---|---|---|---|
| 1 | —$CH_3$ | H | H |
| 2 | H | —$CH_3$ | H |

The results were as follows:

| Compound No. | Percent Stimulation |
|---|---|
| 1 | 20 |
| 2 | 71 |

The compounds of Formula I can be used to promote lipolysis in swine by administering an effective amount of one or a mixture of two or more of the compounds orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the compound needed to promote lipolysis will depend upon the particular compound used, and the particular animal being treated. However, in general, satisfactory results are obtained when the compounds are administered in a dosage of from about 1 to about 500 milligrams per kilogram of the animal's body weight. The compound can be administered in a single dose or in a series of doses in the same day, or over a period of days. For any particular animal, a specific dosage regimen should be adjusted according to the individual need, the particular compound(s) used as the promoters and the professional judgment of the person administering or supervising the administration of the promoter. It is to be understood that the dosages set forth herein are exemplary only, and that they do not, to any extent, limit the scope or practice of the invention.

I claim:

1. A method of promoting lipolysis in swine which comprises administering, to a pig in need of such treatment, orally or parenterally, an effective dosage of a compound of the formula:
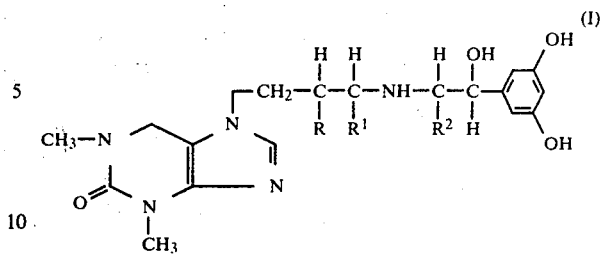
wherein both of R and R¹ are hydrogen, or one is methyl or hydroxyl and the other is hydrogen, and R² is hydrogen or methyl, and their physiologically acceptable acid addition salts.
* * * * *